US008465783B2

(12) United States Patent
Paikin et al.

(10) Patent No.: US 8,465,783 B2
(45) Date of Patent: Jun. 18, 2013

(54) PRODUCTION OF POTASSIUM MAGNESIUM CITRATE AND ITS APPLICATIONS

(75) Inventors: Michael Paikin, Yoqneam Illit (IL); Nissim Guigui, D.N. Misgav (IL)

(73) Assignee: Gadot Biochemical Industries Ltd., Haifa Bay (IL)

( * ) Notice: Subject to any disclaimer, the term of this patent is extended or adjusted under 35 U.S.C. 154(b) by 199 days.

(21) Appl. No.: 12/995,493

(22) PCT Filed: Jun. 2, 2009

(86) PCT No.: PCT/IL2009/000548
§ 371 (c)(1),
(2), (4) Date: Dec. 1, 2010

(87) PCT Pub. No.: WO2009/147667
PCT Pub. Date: Dec. 10, 2009

(65) Prior Publication Data
US 2011/0081456 A1 Apr. 7, 2011

(30) Foreign Application Priority Data
Jun. 2, 2008 (IL) .......................................... 191876

(51) Int. Cl.
*A23L 1/304* (2006.01)
(52) U.S. Cl.
USPC ............. 426/74; 426/519; 426/580; 426/590; 426/599
(58) Field of Classification Search
USPC .................... 426/74, 590, 599, 580, 519, 443
See application file for complete search history.

(56) References Cited

U.S. PATENT DOCUMENTS

| 4,551,342 A * | 11/1985 | Nakel et al. ................... 426/548 |
| 4,582,709 A | 4/1986 | Peters et al. |
| 4,738,856 A | 4/1988 | Clark |
| 4,867,989 A | 9/1989 | Silva et al. |
| 4,895,980 A | 1/1990 | Walsdorf et al. |
| 4,985,593 A | 1/1991 | Walsdorf et al. |
| 5,219,889 A | 6/1993 | Walsdorf et al. |
| 5,432,200 A | 7/1995 | Walsdorf et al. |
| 6,287,607 B2 | 9/2001 | Pak et al. |
| 6,616,955 B2 | 9/2003 | Nunes et al. |
| 7,091,246 B2 | 8/2006 | Rushforth |
| 2005/0180962 A1* | 8/2005 | Raz et al. ................... 424/93.45 |
| 2005/0197402 A1 | 9/2005 | Rushforth |
| 2007/0003613 A1 | 1/2007 | Christy et al. |
| 2008/0193525 A1* | 8/2008 | Pak .............................. 424/464 |

FOREIGN PATENT DOCUMENTS

| DE | 202006012450 U1 | 10/2006 |
| WO | 2007/107999 A1 | 9/2007 |

OTHER PUBLICATIONS

Ruml, et al., "The effect of varying molar ratios of potassium-magnesium citrate on thiazide-induced hypokalemia and magnesium loss," Journal of Clinical Pharmacology, (1998), pp. 1035-1041, vol. 38, No. 11.
Zerwekh, et al., "Reduction of renal stone risk by potassium-magnesium citrate during 5 weeks of bed rest," Journal of Urology, (2007), pp. 2179-2184, vol. 177, No. 6.
Plazman, "Magnesium Madness," The World of Food Ingredients, (Sep. 2000), XP002538319, pp. 72-73.
Marktl, "Physiologie der Interaktion zwischen Kalium und Magnesium," Journal für Mineralstoffwechsel, (2003), vol. 10, No. 1, pp. 5-7, XP0002538320.
"Magnesium Potassium Citrate as a source of magnesium and potassium in food for particular nutritional uses, food supplements and foods intended for the general population," The EFSA Journal, (2006), vol. 392, pp. 1-6, XP002538339.
Anonymous, "Marketing Information," Gadomag K, pp. 1-9, retrieved from the Internet: http://www.gadotbio.com/var/124/11017-Gadomag%20k%20info.pdf> (retrieved on Jul. 22, 2009).
"Gadomag K," pp. 1-5, XP002538340, retrieved from the Internet: http://www.gadotbio.com/var/124/133446-Gadomag%20k.pdf> (retrieved on Jul. 22, 2009).
Wuermser, et al., "Potassium-magnesium citrate versus potassium chloride in thiazide-induced hypokalemia," Kidney International, (2000), pp. 607-612, vol. 57.

* cited by examiner

*Primary Examiner* — Helen F Heggestad
(74) *Attorney, Agent, or Firm* — Browdy and Neimark, P.L.L.C.

(57) ABSTRACT

Provided is a magnesium rich composition including potassium, magnesium and citrate, a method for producing such a composition and food or nutritional product including the composition.

23 Claims, No Drawings

PRODUCTION OF POTASSIUM MAGNESIUM CITRATE AND ITS APPLICATIONS

This is a National Phase Application filed under 35 U.S.C. 371 as a national stage of PCT/IL2009/000548, filed on Jun. 2, 2009, an application claiming the benefit of Israeli Patent Application No. 191876, filed on Jun. 2, 2008, the content of each of which is hereby incorporated by reference in its entirety.

FIELD OF THE INVENTION

This invention relates to a process for the production of potassium magnesium citrate and its uses.

BACKGROUND OF THE INVENTION

The following references are considered to be relevant for an understanding of the invention.

REFERENCES

1. U.S. Pat. No. 4,985,593, Walsdorf et al, "Magnesium Potassium Citrate",
2. U.S. Pat. No. 5,219,889, Walsdorf et al, "Dietary supplementation with potassium Magnesium Citrate",
3. U.S. Pat. No. 7,091,246, Rushforth, "Dietary supplementation with stoichiometrically specific potassium magnesium citrate".
4. U.S. Pat. No. 6,287,607, Pak et al, "Potassium calcium citrate compositions and methods therefore."
5. U.S. Pat. No. 4,551,342, Nakel et al, "Beverages containing specific cation-edible acid mixtures for improved flavor impression"
6. U.S. Pat. No. 5,432,200, Walsdorf et al., "Method for increasing urinary excretion of electrolytes"
7. U.S. Pat. No. 4,867,989, Silva et al., "Chewing gum mineral supplement"
8. U.S. Pat. No. 4,738,856 from Apr. 19, 1988, Clark "Beverages and method for making a beverage for the nutritional supplementation of calcium in humans"
9. U.S. Pat. No. 4,582,709, Peters et al., "Chewable mineral supplement"
10. "The effect of varying molar ratios of potassium magnesium citrate on thiazide-induced hypokalemia and magnesium loss", Ruml Wuermster, Poindexter and Pak, Journal of clynical pharmacology (1998), 38 (11), 1035-1041.
11. "Reduction of renal stone risk by potassium-magnesium citrate during 5 weeks of bed rest" Zerwekh, Odvina, Wuermser, Pak, Journal of Urology (2007), 177 (6) 2179-2184.
12. US 20070003613 A1, Christhy et al, "Preparation to support maintanence of acid-alkaline balance in the human body and methods directed to using same".
13. DE 202006012450 U1, "Soft drink base concentrate and beverage with base-forming minerals"
14. US 20050197402, Rushforth Dennis, "Dietary supplementation with stoichiometrically specific potassium magnesium citrate".
15. U.S. Pat. No. 4,895,980, Walsdorf et al, "Method of manufacturing magnesium potassium citrate"
16. U.S. Pat. No. 6,616,955, Nunes et el, "Beverage compositions comprising palatable calcium and magnesium sources".

SUMMARY OF THE INVENTION

The present invention is directed to compositions comprising edible magnesium that are stable in food and beverages. The composition is comprised of magnesium, potassium and citrate as the active components. It is based on the fact that increasing the magnesium quantity, i.e. molar ratio, relative to that of the potassium in such a three-component system from 1:4 as previously known to 1:1 or 2.5:1 yields a composition that is more efficient for increasing the magnesium intake. The magnesium comprising compositions of the present invention are stable, in various forms of foods, as well as in protein containing beverages, or in their concentrates, and do not separate out of the liquid phase even under long storage periods. The magnesium comprising composition of the present invention is palatable and does not affect the organoleptic properties of the beverage or beverage concentrate to which it is introduced and thus serves as an effective magnesium supplement (fortifier) for beverages and solid food.

Thus the present invention is directed to a dry magnesium rich composition comprising:
(i) at lease one source of magnesium;
(ii) at least one source of potassium; and
(iii) at least one source of citrate;
wherein the composition has a bulk density of 0.35 to 0.75 g/cm$^3$ and comprises 8% to 15% (wt/wt) magnesium and 7.5% to 16% (wt/wt) of potassium on dry weight basis. More preferably the composition comprises 9% to 13% (wt/wt) magnesium and 8% to 12% potassium (wt/wt) on a dry basis and the bulk density is 0.55 to 0.65 g/cm$^3$. The citrate comprises 75% to 80% on a dry basis.

The composition may further comprise artificial or natural coloring agents, emulsifiers, taste modifiers, or other food additives such as food preservatives and stabilizers. In particular, the magnesium rich composition of the invention is used to enrich beverages with magnesium, especially milk, milk-like beverages, soy-milk and naturally or artificially fortified protein containing beverages. It may be either soluble in the beverage or exist as a suspended addition. The magnesium enriched composition introduced into a beverage is stable for a period of at least 90 days wherein less than 5% (wt/wt) of the composition sediments out of the beverage. It should be noted that "stable" relates to the fact that the magnesium enriched composition remains within the liquid phase substantially without sedimenting out. By "substantially without" it is meant that less than 5% of the composition is precipitated. Remaining within the liquid means at least one of remaining suspended, remaining dissolved and remaining bound to a suspended solid or liquid.

The magnesium source is selected from the group consisting of magnesium hydroxide, magnesium oxide, magnesium carbonate, magnesium citrate, or their mixtures.

The citrate source is selected from the group consisting of citric acid, citric acid monohydrate, citric acid mono-, di- or tri-sodium salt, citric acid mono-, di- or tri-potassium salt or ammonium citrate.

The at least one potassium source is selected from the group consisting of potassium hydroxide, potassium citrate, potassium bicarbonate or their mixtures.

In accordance with the present invention, the magnesium enriched dry composition of the present invention may comprise a molar ratio magnesium:potassium: citrate of 1:1:1 or 5:2:4.

The invention is further directed to a method for producing a dried magnesium-rich composition comprising:
(i) dissolving at least one source of citrate in water, agitating and cooling;
(ii) adding at least one source of magnesium and at least one source of potassium the agitated cooled aqueous solution; and (ii) drying the aqueous magnesium solution so as to produce the dried magnesium-rich composition, wherein said composition comprises at least 8% magnesium on a dry weight basis, and at least 7.5% potassium on a dry weight basis.

The invention is further directed to foods or nutritional product comprising the magnesium enriched composition. The nutritional product may be a beverage or beverage concentrate comprising the magnesium enriched composition. In particular, the beverages are milk and milk-like based beverages that may be fortified with proteins, vitamins, minerals or their mixtures. Non-limiting examples of beverages are selected from soy milk, cow milk, camel milk, goat milk, or their mixtures and fermented milk based products like yoghurts. Such beverages may further comprise additional edible supplements selected from cocoa, vanilla, fruit or vegetable concentrates or flavorings.

DETAILED DESCRIPTION OF EMBODIMENTS

The present invention is thus directed to compositions comprising magnesium, which are stable in food and beverages and in food and beverage supplements. The compositions comprise a relatively high molar ratio of magnesium to potassium, e.g. about 1:1 to about 2.5:1. Preferably the compositions are suitable for use in milk, soy milk and other "milk-like", "milk-containing", protein containing beverages or their mixtures. Despite the large number of supplements currently available and known in the art, many of these supplements are unstable and precipitate out of solution over time. A rather severe limitation associated with the use of magnesium sources in food and beverages occurs in protein-containing beverages. This is due to the fact that in case the magnesium source is soluble, ions of $Mg^{2+}$ will interact with proteins during heat treatment (UHT or pasteurization); while in case the magnesium source is an insoluble source, the material will gradually precipitate during the shelf life. Slowing down precipitation is not easily achieved and different types of hydrocolloids are usually applied for such a purpose of maintaining the magnesium evenly distributed in solution or in the food to which it was added.

The products of the present invention may be used to meet the demand in the market for stable sources of magnesium, which are suitable for adding to foods and beverages. The products of the present invention are used as supplements and do not affect the organoleptic properties or the taste of the food or beverage to which they are added. The magnesium products of the present invention are both stable and do not typically precipitate during the storage of the food/beverage even after storage periods of about 90 days. Consequently, usage of hydrocolloids for slowing down precipitation is not required for the products of the present invention.

The present invention relates in particular to stable dried compositions of organic magnesium, in the form of magnesium potassium citrate, to methods for the preparation of these compositions and their use as magnesium supplements. The products of this invention may be in the form of a solid such as a powder, flakes, granules, a liquid such as a liquid concentrate, suspension, microemulsion. Such products may be consumed either directly for enhancing uptake of magnesium or as an additive in various food and beverages to fortify these food products with magnesium. The compositions in any of the above-mentioned forms are stable in beverages and in food, to which they added.

The compositions of the present invention exhibit high bioavailability. The compositions of the present invention are stable in sterilization and pasteurization processes known in the art of food and beverage processing. The composition of the present invention does not require the co-addition of other agents in order to retain the magnesium in a stable suspension. Notwithstanding, the composition may further comprise artificial or natural coloring agents, emulsifiers, taste modifiers, or other food additives such as food preservatives.

A non limiting process for producing a dried magnesium-rich composition according to the present invention is herein displayed.

In a first mixing step citric acid or salts thereof is dissolved in dionized water using agitation to form an aqueous solution having citric acid or its salts typically in a concentration range of 0.25 to 1.2 M. Non limiting sources of citrate source is selected from the group consisting of citric acid, citric acid anhydrous, citric acid monohydrate, citric acid mono-, di- or tri-sodium salt, citric acid tripotassium salt or ammonium citrate. The aqueous solution is cooled to a set temperature below 25° C. Cooling jackets known in the art, may be employed on a large scale, or the vessel may be at least partially immersed in a water bath on the small scale, as is known in the art. In the present invention different chillers were used (such as CH10TR nameplate number 30089, Unique, Nehalim, Israel or CC230, Huber High Precision Thermoregulation, Offenburg, Germany)

To the agitated cooled aqueous solution containing citric acid or salts thereof are added about 2-7 moles of magnesium and about 2.5-3 moles of potassium. Typically this step is performed in a standard mixed vessel well known in the art. This mixing step typically takes up to 30 minutes while the vessel is cooled. The range of final pH prior to drying process is 7.5-10.5. The reaction can be performed at different concentration of the reagents, but preferable range of TDS prior to drying is 25-35%.

Non limiting examples of magnesium used are selected from the group consisting of magnesium hydroxide, magnesium oxide, magnesium carbonate, magnesium citrate, or their mixtures. Non limiting examples of potassium used are selected from the group consisting of potassium hydroxide, potassium citrate, potassium bicarbonate or their mixtures.

Typically the potassium salt is added in to produce the molar ratio of potassium to citrate in a range of 0.5-1. Typically the magnesium salt is added in suitable concentration to produce the molar ratio of Magnesium and Citrate in range of 1-1.25.

In the drying step, the aqueous solution is dried and liquid is removed therefrom to form a dry magnesium potassium citrate composition. Typically drying is done using a spray drying or freeze drying process in a dryer APV PSD52 (APV Nordic Anhydro, Silkeborg, Denmark) using the inlet air with temperature from 190 up to 350° C. as is known in the art. Excess liquid is removed from the solution until a solid phase forms. The solid phase may be in the form of a powder, flakes, granules or other solid form. The resultant solid composition may then be suitably stored and/or packaged in either a solid form or in a liquid form (dissolved or suspended). The resultant composition typically has a bulk density of about 0.55 to 0.65 $g/cm^3$, more typically, about 0.6 $g/cm^3$.

The obtained dry magnesium-potassium-citrate composition typically has a composition as is shown in the Table below.

TABLE 1

Typical Composition of a magnesium-potassium-citrate composition on a Dry Weight Basis*

| COMPONENT | RELATIVE MOLAR RATIO | PERCENT OF DRY COMPOSITION [WT/WT %] |
|---|---|---|
| CITRATE | 1-2 | 75-80 |
| MAGNESIUM | 1-2.5 | 9-13 |
| POTASSIUM | 1 | 8-16 |

*it should be noted that the "dry weight" was calculated excluding up to 10% adsorbed water in the product

EXAMPLES

Example 1

Method of preparation of Magnesium Potassium Citrate with a molar ratio of Mg, K and Citrate ions 1:1:1.

332.5 g of Citric acid anhydrous were dissolved in 1840 g water; while agitated and cooled 82 g magnesium Oxide and 158 g potassium hydroxide were added. The mixture was dried in the spray dryer. Obtained material was analyzed exhibiting the following properties:
Bulk density—0.6 kg/l; Mg content—9.5%; K content—10%

Example 2

Method of preparation of Magnesium Potassium Citrate with a molar ratio of Mg, K and Citrate ions 5:2:4.

540 g of Citric acid anhydrous were dissolved in 2840 g water; while agitated and cooled 141 g magnesium Oxide and 107 g potassium hydroxide were added. The mixture was dried in the spray dryer. Obtained material was analyzed exhibiting the following properties:
Bulk density—0.6 kg/l; Mg content—12.5%; K content—8.2%

Example 3

Use for Fortifying Beverage 3 g of material obtained in Example 1 were added to 1 liter of Soy milk during agitation. Mg content was tested and found 445 mg/l. After retention of two days without agitation the Mg content in upper layer was tested again and found 444 mg/l.

Example 4

Use for Fortifying Beverage 3 g of material obtained in Example 2 were added to 1 liter of Soy milk during agitation. Mg content was tested and found 547 mg/l. After retention of two days without agitation the Mg content in upper layer was tested again and found 545 mg/l.

Example 5

Use for Fortifying Beverage 3 g of material obtained in Example 1 were added to 1 liter of cow milk during agitation. Mg content was tested and found 297 mg/l. After retention of two days without agitation the Mg content in upper layer was tested again and found 289 mg/l.

Example 6 usage of KMgCitrate in Molar Ratio of 4:1:2

Potassium magnesium citrate was prepared according to U.S. Pat. No. 4,985,593. 5.6 g Of the prepared material were added to 1 liter of soy milk and the samples stored refrigerated. After 48 hours of retention, Mg content was tested in the upper level and was found 372 mg/liter while initial concentration of Mg was 373 mg/liter.

Example 7

Usage of Tri Magnesium Citrate 2.2 g of Tri magnesium citrate nona hydrate were added to 1 liter of soy milk during the agitation. Magnesium content was tested and found 475 mg/l. After retention of two days without agitation the Mg content in upper layer was tested again and found 307 mg/l. 35 percents of Magnesium sediment during two days.

Example 8

Usage of Tri Magnesium Citrate+Carragenan 2.2 g of Tri magnesium citrate nona hydrate and 0.2 g of Kappa Carragenan were added to 1 liter of soy milk during the agitation. Magnesium content was tested and found 471 mg/l. After retention of two days without agitation the Mg content in upper layer was tested again and found 351 mg/l. 25 percents of Magnesium sediment during two days.

Example 9

Usage of Mixture Tri Potassium Citrate+Tri Magnesium Citrate 2.2 g of Tri magnesium citrate nona hydrate and 2.2 g of tri potassium citrate were added to 1 liter of soy milk during the agitation. Magnesium content was tested and found 476 mg/l. After retention of two days without agitation the Mg content in upper layer was tested again and found 418 mg/l. 12 percents of Magnesium sediment during two days.

Example 10

120 g of material obtained in Example 1 were added to 40 liters of soy milk, after agitation the mixture passed the well known (in the art) UHT treatment and samples were collected and stored refrigerated. The Magnesium content in the upper level of sample was tested during 13 weeks and the results are as following:
initial Mg content—468 mg/l
after 1 week—471 mg/l
after 2 weeks—470 mg/l
after 3 weeks—471 mg/l
after 4 weeks—470 mg/l
after 5 weeks—462 mg/l
after 6 weeks—468 mg/l
after 7 weeks—470 mg/l
after 8 weeks—468 mg/l
after 9 weeks—467 mg/l after 10 weeks—465 mg/l
after 11 weeks—471 mg/l
after 12 weeks—465 mg/l
after 13 weeks—466 mg/l

The invention claimed is:

1. A magnesium rich composition, comprising:
    (i) at least one source of magnesium;
    (ii) at least one source of potassium; and
    (iii) at least one source of citrate;
    wherein the composition has a bulk density of 0.35-0.75 g/cm$^3$ and comprises from about 8% to about 15% (wt/wt) magnesium and from about 7.5% to about 16% (wt/wt) potassium and 75% to 80% citrate on dry weight basis and having pH of about 7.5-10.5.

2. The composition according to claim 1, comprising 9% to 13% (wt/wt) magnesium and about 8% to 12% (wt/wt) potassium on a dry basis, having a bulk density of 0.55 to 0.65 g/cm$^3$.

3. The composition according to claim 1, wherein the magnesium source is selected from the group consisting of magnesium hydroxide, magnesium oxide, magnesium carbonate, magnesium citrate, and any mixture thereof.

4. The composition according to claim 1, wherein the citrate source is selected from the group consisting of citric acid, citric acid anhydrous, citric acid monohydrate, citric acid mono-, di- or tri-sodium salt, citric acid tripotassium salt, and ammonium citrate.

5. The composition according to claim 1, wherein the source of potassium is selected from the group consisting of potassium hydroxide, potassium citrate, potassium bicarbonate, and any mixture thereof.

6. The composition according to claim 1, wherein the potassium source is potassium hydroxide or potassium oxide; the magnesium is magnesium oxide or magnesium hydroxide; and the citrate is citric acid anhydrous or monohydrate.

7. The composition according to claim 6, comprising a molar ratio of magnesium:potassium:citrate of 1:1:1.

8. The composition according to claim 6, comprising a molar ratio of magnesium:potassium:citrate of 5:2:4.

9. The composition according to claim 1, further comprising stabilizers, coloring agents or emulsifiers.

10. The composition according to claim 1, in a dry form selected from the group consisting of powder, granules, and flakes.

11. The composition according to claim 1, dissolved or suspended in an aqueous based solution.

12. A food or nutritional product comprising a composition according to claim 1.

13. The product according to claim 12, being a beverage.

14. The product according to claim 13, wherein the beverage is a natural based beverage or a non-natural based beverage.

15. The product according to claim 14, wherein the natural based beverage is a fruit or vegetable based beverage or a milk based beverage.

16. The product according to claim 15, wherein the milk based beverage is selected from the group consisting of a soy milk beverage, reconstituted milk formula beverage, goat milk beverage, sheep milk beverage, camel milk beverage, substitute milk beverage, cow milk beverage, oat milk beverage, human milk beverage, and any mixture thereof.

17. The product according to claim 14, further comprising one or more of a flavoring, vitamin, mineral, and protein.

18. The product according to claim 14, comprising at least 2 g/L to 6 g/L of the magnesium rich composition.

19. The product according to claim 14, being stable for a period of at least 90 days.

20. A method for producing a dried magnesium-rich composition, having a bulk density of 0.35-0.75 g/cm$^3$ and a pH of about 7.5-10.5 comprising:
    (i) dissolving at least one source of citrate in water, agitating and cooling to produce an agitated cooled aqueous solution;
    (ii) adding at least one source of magnesium and at least one source of potassium to the agitated cooled aqueous solution to produce an aqueous magnesium solution; and
    (ii) drying the aqueous magnesium solution to produce the dried magnesium-rich composition, wherein the composition comprises at least 8% magnesium on a dry weight basis, and at least 7.5% potassium on a dry weight basis.

21. The composition of claim 1, being suitable for fortifying a protein-containing food or beverage.

22. The composition of claim 1, being suitable for preparing a stable protein-containing food or beverage.

23. A method for fortifying a food or beverage which comprises adding the composition of claim 21 to a food or beverage.

* * * * *